United States Patent [19]
Delson

[11] Patent Number: 5,394,989
[45] Date of Patent: Mar. 7, 1995

[54] CASTLE WITH STORAGE COMPARTMENT

[76] Inventor: Donn M. Delson, 29665 Kimberly Dr., Agoura Hills, Calif. 91301

[21] Appl. No.: 142,835

[22] Filed: Oct. 25, 1993

Related U.S. Application Data

[63] Continuation-in-part of Ser. No. 918,245, Jul. 23, 1992, abandoned.

[51] Int. Cl.$^6$ ............................................. B65D 25/16
[52] U.S. Cl. .................................. 206/457; D6/434; D9/322; 206/83; 446/76
[58] Field of Search ............... D3/39, 66, 78; D9/322; 206/6.1, 63.5, 83, 457, 566; 229/8; 383/75; 446/71, 75–77, 80; D6/434

[56] References Cited

U.S. PATENT DOCUMENTS

| | | | |
|---|---|---|---|
| D. 37,342 | 2/1905 | Dzubay | D6/434 |
| D. 123,428 | 11/1940 | Buckingham | D9/322 |
| D. 132,904 | 6/1942 | Buckingham | D9/322 |
| D. 138,602 | 8/1944 | Merralls | D9/322 |
| D. 176,370 | 12/1955 | Natale | D9/322 |
| D. 188,135 | 7/1960 | Koenig | D9/322 |
| D. 199,042 | 9/1964 | Douglas | D9/322 |
| 305,674 | 9/1884 | Dalzell | 220/4.21 |
| D. 305,698 | 1/1990 | Chen | D9/322 |
| 1,698,731 | 1/1929 | Otto | 206/457 |
| 1,946,250 | 2/1934 | Whaley | 446/76 |
| 2,061,510 | 11/1936 | Drumpelmann | 229/8 |
| 2,565,283 | 8/1951 | Throckmorton | 383/75 |
| 3,389,851 | 6/1968 | Clark | 220/4.21 |
| 3,400,485 | 9/1968 | Callin et al. | 446/76 |
| 3,832,800 | 9/1974 | Selesny | 446/77 |
| 4,014,450 | 3/1977 | Girotti | 220/354 |
| 4,058,214 | 11/1977 | Mancuso | 220/4.21 |
| 4,061,241 | 12/1977 | Retelny | 220/4.25 |
| 5,074,417 | 12/1991 | Kenny | 206/457 |

FOREIGN PATENT DOCUMENTS

| | | | |
|---|---|---|---|
| 1452212 | 8/1966 | France | 446/71 |

Primary Examiner—Jimmy G. Foster
Attorney, Agent, or Firm—Christie, Parker & Hale

[57] ABSTRACT

A miniature castle structure comprised of an upper castle top portion, a lower castle base portion and a supple cloth sack. A storage compartment is formed by the lower base portion and the upper castle top portion. The cloth sack, which stores the broken teeth, is held within the space cavity of the containment device. A raised surface beneath the upper castle portion secures the castle top in place along the ledge that surrounds the open face end of the castle base. Thus, the castle structure provides a distinctive means of storing the containment that is used in conjunction with the Tooth Fairy bedtime story.

6 Claims, 2 Drawing Sheets

5,394,989

CASTLE WITH STORAGE COMPARTMENT

CROSS-REFERENCE TO RELATED APPLICATION

This is a continuation-in-part of application Ser. No. 07/918,245, filed Jul. 23,1992, abandoned.

BACKGROUND OF THE INVENTION

The present invention relates to miniature dwelling structures and, more particularly, to a miniature castle that may be used as a containment for concealing a tooth storage device.

The Tooth Fairy bedtime story was created about a hundred-years ago in an effort to ease the anxiety children experienced while losing their infant teeth. After losing a tooth, a child would typically leave the broken tooth under a pillow, or in a bedside glass, and await the coming of the Tooth Fairy. During the night while the child was sleeping, the tooth would be replaced with either money or a present.

When children became older, they inevitably discovered that their parents were actually the gift-bearers. As expected, the Tooth Fairy suffers the same ill fate as do Santa Claus and the Easter Bunny. Nevertheless, the loss of a tooth and the coming of the Tooth Fairy represent an important time for children as they begin to notice the changes that are occurring in their bodies.

The entire process of removing a tooth and replacing it with something in return has proven to be a formidable task for parents. At the same time, there exists a special childhood meaning attached to the loss of a tooth and the coming of the Tooth Fairy. Thus, a keepsake to serve as a memento for such an occasion has great appeal.

SUMMARY OF THE INVENTION

The present invention is a keepsake to serve as a memento for the coming of the Tooth Fairy in the form of a castle, which provides a new and useful means of exchanging a tooth for money, or a small present. A cloth pouch, which contains small articles, is stored within the interior space cavity of the castle base. The castle top portion covers and rests upon the supporting ledge surrounding the open face of the lower castle base portion.

One aspect of the invention is a castle structure storage device that provides the means for a tooth to be readily exchanged with either money or a small present. The device comprises of a concealed storage cavity space within a castle base portion formed in the exterior shape of a castle base.

A ledge surrounding the open face of the castle base supports the upper castle top division. The size of the aperture formed by the ledge is substantially the same size as the raised surface below the castle top portion. In order to secure the upper portion in place, the raised surface underneath the castle top rests in a well formed by the inner side walls of the castle base ledge.

Another aspect of the invention is an upper portion that is in the form of a castle top. The castle top is removable and provides access to the concealed storage compartment within the castle base. The formed base of the castle top securely rests upon the supporting ledge of the castle base and covers the storage cavity space within the lower castle base portion.

BRIEF DESCRIPTION OF THE DRAWINGS

The features of a specific embodiment of the best mode contemplated of carrying out the invention are illustrated in the drawings, in which.

DETAILED DESCRIPTION

Figure 1:
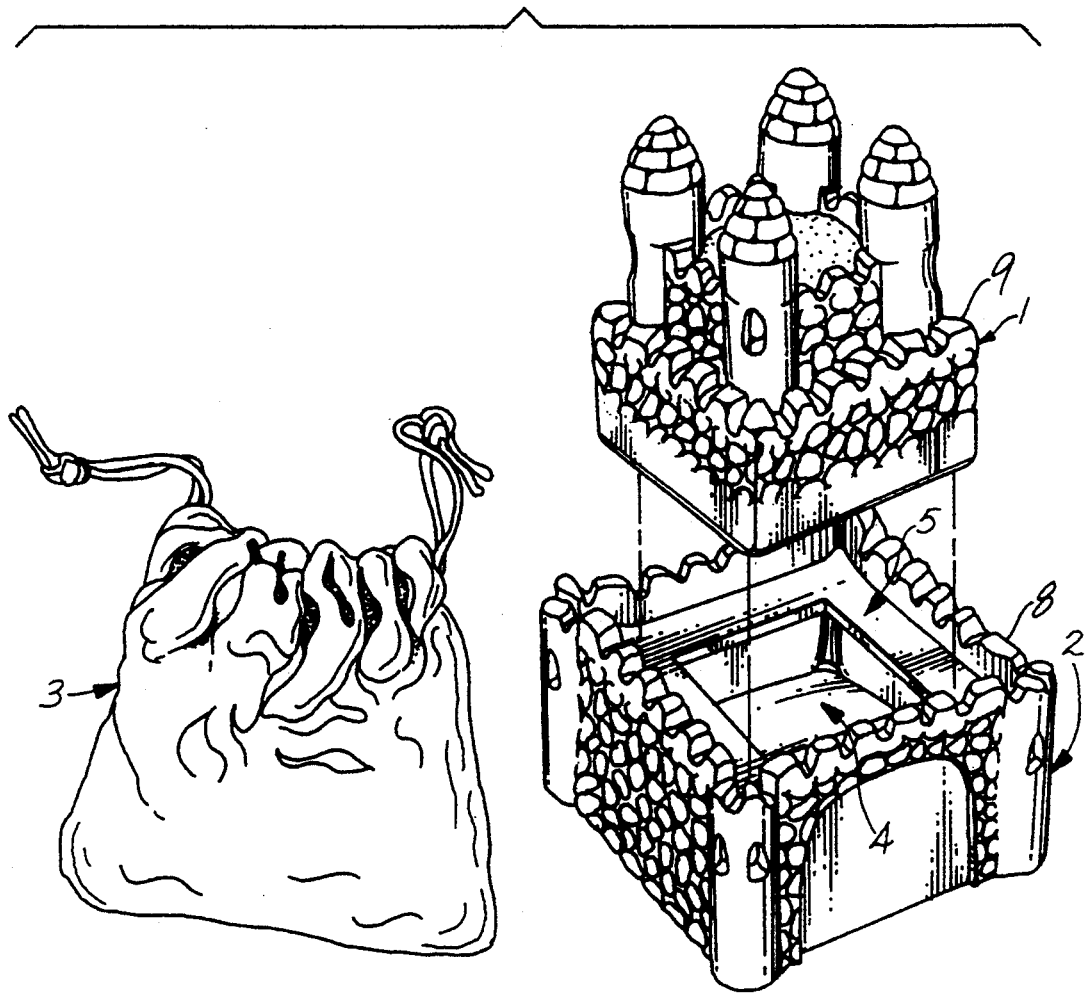
FIG. 1 is an exploded perspective view of the upper castle top portion and the lower castle base portion of the storage device and a front view in elevation of the cloth sack.

In FIG. 1 a castle structure storage device comprises an upper castle top portion 1, a lower castle base portion 2 and a cloth sack 3. Portions 1 and 2 are generally square in shape. The cloth sack 3 serves as a container for a child's broken tooth and is stored within the inner cavity 4 of the lower castle base portion 2.

The outer layer of the lower base portion 2 in FIG. 1 simulates the appearance of a stone castle. A pattern of extensions, grooves and notches along the outer surface of the base portion 2 characterizes the overall structure of a castle dwelling base. The castle base 2 includes surface markings that imitate the stone construction of a castle dwelling. Lookout towers, which are also characteristic of a castle structure, are included along the outer points of the castle base 2. The lower castle base portion 2 has four side faces, a bottom face and an open top face. A supporting ledge 5 surrounding the open face side of the base portion 2 serves as a seat for the upper castle portion 1. Battlements 8 are formed around the top edge of base portion 2 above ledge 5.

The upper portion 1 of the storage device in FIG. 1 has an appearance of a castle structure. The outer castle top 1 also includes surface markings that imitate the stone construction of a castle. A pattern of extensions, grooves and notches along the outer surface of the upper portion 1 characterizes the overall structure of a castle dwelling top. The top portion 1 also has lookout towers that are characteristic of a stone castle. Battlements 9 are formed around the middle of top portion 1 below the lookout towers.

Figure 2:
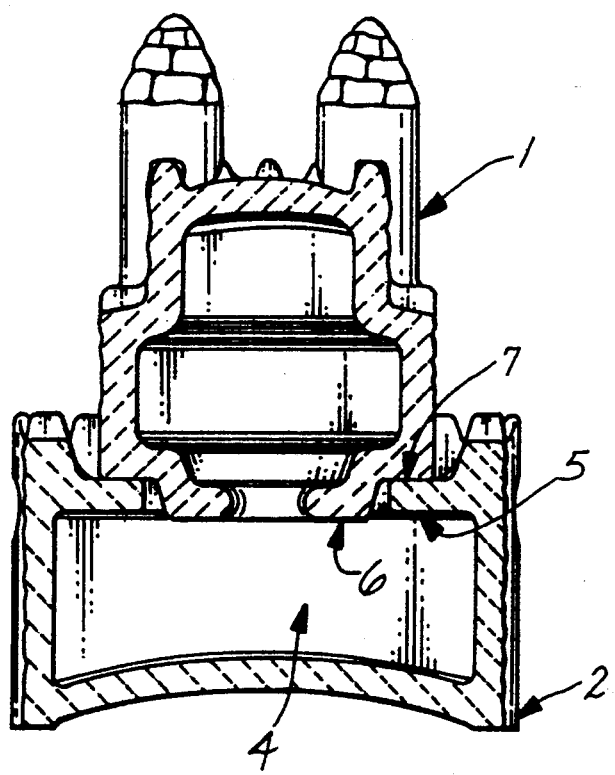
FIG. 2 is a side elevation cut-away view illustrating the interior space cavity of the castle structure storage device.

In FIG. 2, a raised surface 6 is projected from bottom face of the castle top portion 1. The raised surface 6 has similar dimensions to that of the opening located on the top face of the lower base portion 2. A well is formed by the sides of the ledge 5 surrounding the open face of the lower base portion 2 that seats the raised surface 6 beneath the castle top 1. The outer remaining surface of the bottom face of the upper castle portion 1 directly rests upon the base portion ledge 5. The junction between the top and the base forms a battlement around the base which camouflages the junction to thereby conceal the interior compartment as shown in FIG. 2.

The storage compartment within the castle base portion 2 in FIG. 2 is enclosed by the castle top 1. A cavity space 4 is formed by the internal bottom face and sides of the lower portion 2, and by the raised surface 6 of the upper castle portion. The storage space is of sufficient volume to house the cloth sack 3 that contains the broken tooth.

What is claimed is:

1. A castle structure adapted to function as a storage device comprising:
   a concealed storage compartment having an inner cavity, having four side faces, a bottom face and an open top face, formed in a structure having the exterior shape of a castle base;

a supporting ledge extending perpendicular to the four side faces inside the castle base;

a removable covering formed in the exterior shape of a castle top, wherein the removable covering seats onto the ledge of the castle base forming a battlement; and a plush cloth sack with an open end sealed by a drawstring being located in the concealed storage compartment.

2. The storage device of claim 1 in which the cloth sack serves as a containment for a tooth.

3. The storage device of claim 1 in which the removable covering has a formed base with a raised surface that rests upon the supporting ledge of the base storage compartment.

4. The keepsake of claim 1, in which the outer surface of the base and the covering simulate a stone facade.

5. The keepsake of claim 4, in which the base and the covering have four corners and turrets formed at the four corners.

6. The keepsake of claim 1, in which the ledge is spaced downwardly from the top edge of the base so the sides of the base surround and constrain the covering when the covering fits on the base.

* * * * *